United States Patent [19]

Rebhahn et al.

[11] Patent Number: 4,537,971

[45] Date of Patent: Aug. 27, 1985

[54] PROCESS FOR PREPARING QUINOLINIC ACID

[75] Inventors: Robert W. J. Rebhahn, West Chester, Ohio; James E. Kassner, Fort Mitchell, Ky.; Raymond E. Werner, Cincinnati, Ohio

[73] Assignee: The Hilton-Davis Chemical Co., Cincinnati, Ohio

[21] Appl. No.: 536,133

[22] Filed: Sep. 26, 1983

Related U.S. Application Data

[63] Continuation of Ser. No. 261,254, May 6, 1981, abandoned.

[51] Int. Cl.$^3$ ............................................. C07D 213/55
[52] U.S. Cl. ...................................... 546/320; 546/5; 546/321
[58] Field of Search ............................ 546/320, 321, 5

[56] References Cited

U.S. PATENT DOCUMENTS 2,347,410  4/1944  Hawkinson et al. ............... 546/5 X
2,371,691  3/1945  Hawkinson et al. .................... 546/5

OTHER PUBLICATIONS

W. Stix and S. Bulgatsch Chemische Berichte 65 11. (1932) [C.A. 26: 2195[1] (1932)] and translation.

*Primary Examiner*—Alan L. Rotman

*Attorney, Agent, or Firm*—Terrence E. Miesle; Paul E. Dupont; B. Woodrow Wyatt

[57]   ABSTRACT

This invention relates to improved processes for the manufacture of quinolinic acid run with a higher concentration of reactants in the initial step wherein quinoline is oxidized with hydrogen peroxide in an aqueous sulfuric acid solution in the presence of copper sulfate to prepare copper quinolinate, and in subsequent steps converting the copper quinolinate from the initial step to quinolinic acid by treating the copper salt with alkali to form the water soluble alkali salt form of quinolinic acid precipitating the copper as insoluble cupric oxide and thereafter treating the soluble alkali salt form with acid to obtain the quinolinic acid, the improvement whereby the reaction of the initial step is carried out in a thermally controllable and safe manner and the formation of by-products is minimized which comprises in the initial step adding separately either in portion-wise multiple and approximately equal portions or adding continuously and simultaneously over a period of time each of the following, the sulfuric acid, the quinoline and the hydrogen peroxide to an aqueous solution of the copper sulfate over such time intervals of sufficient length spaced between each group of portion-wise additions or at such a rate as to allow the hydrogen peroxide to react to maintain an unreacted hydrogen peroxide concentration in the reaction of between approximately three and approximately fifteen percent.

8 Claims, No Drawings

PROCESS FOR PREPARING QUINOLINIC ACID

This application is a continuation, of application Ser. No. 261,254, filed 5/6/81 now abandoned.

BACKGROUND OF THE INVENTION

1. Field of the Invention

This invention relates to improved processes for preparing quinolinic acid, a starting material for the manufacture of nicotinic acid, vitamin B complex, and quinolinic acid anhydride, by first preparing copper quinolinate by oxidizing quinoline with hydrogen peroxide in an aqueous sulfuric acid medium in the presence of a copper sulfate, and in subsequent steps converting said copper quinolinate to quinolinic acid by precipitating the copper as an insoluble salt in an alkaline medium and acidifying the resulting alkaline salt of quinolinic acid.

2. Description of the Prior Art

There are several synthetic routes described in the prior art for the preparation of copper quinolinate and the conversion thereof to quinolinic acid via precipitation of the copper as insoluble cupric salts. One of these routes, and the one in which this invention constitutes an improvement, involves the oxidation of quinoline with hydrogen peroxide in a very dilute aqueous acid medium in the presence of a copper salt and the subsequent conversion to quinolinic acid via alkaline precipitation of the copper as cupric sulfide followed by acidification of the alkaline salt of the quinolinic acid. The following items, which are based on the oxidation of quinoline and subsequent conversion to quinolinic acid, to date appear to constitute the most relevant prior art with regard to the instant invention.

W. Stix and S. A. Bulgatsch in Chemische Berichte, 65, 11 (1932) [Chemical Abstracts 26: 2195[1] (1932)]describe the preparation of copper quinolinate by the oxidation of quinoline. In their process, Stix and Bulgatsch heat a mixture of quinoline, three percent aqueous hydrogen peroxide and 25 percent aqueous copper sulfate solution in one large portion while maintaining a temperature maximum of 70° C. with external cooling. The reaction is maintained at 70° C. for eight hours and additional hydrogen peroxide is added and the temperature maintained. Alkali is added to the solution to reduce the acidity and after heating to 90° C. the reaction is cooled to room temperature to obtain copper quinolinate in 67 percent yield based on the quinoline used. The copper quinolinate was then reacted with ten percent aqueous sodium sulfide, and after the insoluble copper sulfide was removed by filtration, the resulting solution was made acid with sulfuric acid to obtain quinolinic acid of indeterminate purity in 51.5 percent yield based on the quinoline used.

U.S. Pat. No. 2,371,691, which issued Mar. 2, 1945 in the names of A. T. Hawkinson and A. A. Elston, teaches the preparation of copper quinolinate by slowly adding hydrogen peroxide to a solution of quinoline, copper acetate, acetic acid and water at 60° C. at such a rate as to maintain the reaction mixture temperature below 70° C. Copper quinolinate is obtained in 69.1 percent yield based on the quinoline used.

U.S. Pat. No. 2,347,410, which issued Apr. 25, 1944 in the names of A. T. Hawkinson and A. A. Elston, teaches a process for the manufacture of pyridine carboxylic acids, especially quinolinic and nicotinic acids, from their heavy metal salts, especially copper salts. The copper quinolinate dihydrate is first suspended in sufficient water to form a thin slurry and with agitation concentrated ammonium hydroxide is added in a sufficient amount to cause complete solution of the copper quinolinate. The resulting solution is treated with an excess of sodium hydroxide solution. The solution is then heated in the range of 40° to 60° C. to form and precipitate the copper oxide which is collected by filtration. The filtrate containing the alkali salt of quinolinic acid is boiled to remove the excess ammonia. The solution is adjusted to a pH in the range of 3 to 5 with a mineral acid and the resulting solution is evaporated to dryness to obtain a mixture of quinolinic acid and salts.

SUMMARY OF THE INVENTION

The present invention provides for improved processes for the manufacture of quinolinic acid, by preparing copper quinolinate in the initial step by oxidizing quinoline with hydrogen peroxide in an aqueous sulfuric acid solution in the presence of copper sulfate. In subsequent steps, the copper quinolinate is treated with alkali to convert it to its alkali salt form which is then separated from the insoluble cupric oxide. Thereafter the soluble salt form is treated with acid to obtain quinolinic acid. In one of the improved processes, the improvement comprises adding in the initial step separately in a portion-wise manner, and in a multiple of approximately equal proportions, the reaction quantities of the sulfuric acid, the quinoline and the hydrogen peroxide either simultaneously or sequentially. Time intervals between each group of portion-wise additions are adjusted to prevent the resulting exothermic reaction from becoming uncontrolled. In the second of the improved processes, the improvement comprises continuously and simultaneously adding separately in the initial step, the reaction quantities of the sulfuric acid, the quinoline and the hydrogen peroxide to an aqueous solution of the copper sulfate at such a rate as to prevent the resulting exothermic reaction from becoming uncontrolled.

DETAILED DESCRIPTION INCLUSIVE OF THE PREFERRED EMBODIMENTS

The processes heretofore taught in the prior art for the preparation of copper quinolinate, which involve the oxidation of quinoline with hydrogen peroxide in an acidic aqueous medium in the presence of a copper salt, have inherent deficiencies which become readily apparent when the processes are scaled-up to commercial production size batches. One of these deficiencies is the inability to control the heat generated during the extremely exothermic reaction with the simultaneous evolution of carbon dioxide gas from the reaction mixture. Another of the deficiencies is the low concentration of reactants at which the prior art processes are run. This low concentration produces low product output per volume of reactor space leading to higher costs and thus, less commercial feasibility. Hawkinson and Elston increased the volume efficiency and improved the control of the reaction by replacing the sulfuric acid and copper sulfate of the earlier Stix and Bulgatsch process with acetic acid and copper acetate. This afforded control in small laboratory scale reactions, but when scaled-up to a larger pilot plant size reaction, the safety and control of the process required for commercialization were lacking. In addition, the use of the more expensive acetic acid and copper acetate offset the savings resulting from the increased volume efficiency. When the teaching of the prior Stix and Bulgatsch process for oxidizing quinoline with hydrogen peroxide in dilute aqueous sulfuric acid in the presence of copper sulfate was employed, there was obtained a reaction mixture that was highly contaminated and which yielded no quinolinic acid when further reacted as described by those authors.

The instant invention provides for improved processes run with higher concentrations of reactants in an initial step for the oxidation of quinoline with hydrogen peroxide in an aqueous sulfuric acid solution in the presence of copper sulfate which affords improved control and higher volume efficiency of the reaction thus allowing the process to be efficiently and safely scaled-up to commercial size production batches.

More specifically, this invention in the first of its process improvement aspects provides in a process wherein quinoline is oxidized in an initial step with hydrogen peroxide in an aqueous medium in the presence of sulfuric acid and copper sulfate to produce copper quinolinate and in subsequent steps, the copper quinolinate is treated with alkali to convert it to its soluble alkali salt form, which is removed from the insoluble cupric oxide, and thereafter, is treated with acid to produce quinolinic acid, the improvement whereby the reaction of the initial step is carried out in a thermally controllable and safe manner and the formation of by-products is minimized which comprises adding in said initial step separately in a portion-wise manner approximately fifteen to approximately twenty-five approximately equal portions of the reaction quantities of the sulfuric acid, the quinoline and the hydrogen peroxide either sequentially in that order or simultaneously at time intervals of sufficient length spaced between each group of portion-wise additions to allow the hydrogen peroxide to react before the next addition to an unreacted hydrogen peroxide concentration in the reaction mixture of between approximately three and approximately fifteen percent.

A particularly preferred process improvement within the ambit of the first aspect of the instant invention and in the process wherein quinoline is oxidized in an initial step with hydrogen peroxide in an aqueous medium in the presence of sulfuric acid and copper sulfate to produce copper quinolinate and in subsequent steps, the copper quinolinate is treated with alkali to convert said copper quinolinate to its soluble alkali salt form which is removed from the insoluble cupric oxide and is treated with acid to produce quinolinic acid, is the improvement which further comprises utilizing in an initial step a ratio of from approximately four parts to approximately fifteen parts by weight of water for each part by weight of quinoline.

This invention, in the second of its process improvement aspects, provides in a process wherein quinoline is oxidized in an initial step with hydrogen peroxide in an aqueous medium in the presence of sulfuric acid and copper sulfate to produce copper quinolinate and in subsequent steps, the copper quinolinate is treated with alkali to convert said copper quinolinate to its soluble alkali salt form which is removed from the insoluble cupric oxide and thereafter said soluble alkali salt form is treated with acid to produce quinolinic acid, the improvement whereby the reaction of the initial step is carried out in a thermally controllable and safe manner and the formation of by-products is minimized which comprises continuously and simultaneously adding in the initial step separately the reaction quantities of the sulfuric acid, the quinoline and the hydrogen peroxide to an aqueous solution of the copper sulfate at such a rate as to allow said hydrogen peroxide to react to maintain an unreacted hydrogen peroxide concentration in the reaction of between approximately three and approximately fifteen percent.

A particularly preferred process improvement within the ambit of the second process aspect of the instant invention wherein quinoline is oxidized in an initial step with hydrogen peroxide in an aqueous medium in the presence of sulfuric acid and copper sulfate to produce copper quinolinate and in subsequent steps, the copper quinolinate is treated with alkali to convert said copper quinolinate to its soluble alkali salt form which is removed from the insoluble cupric oxide and thereafter said soluble alkali salt form is treated with acid to produce quinolinic acid, is the improvement which further comprises utilizing in the first step a ratio of approximately four parts to approximately fifteen parts by weight of water for each part by weight of quinoline.

Although the invention resides in multi-step processes for the preparation of quinoline, it is readily apparent that the improvement in the processes is contained within the initial step of the processes.

The overall process of the invention is well known and is illustrated by the following reaction sequence:

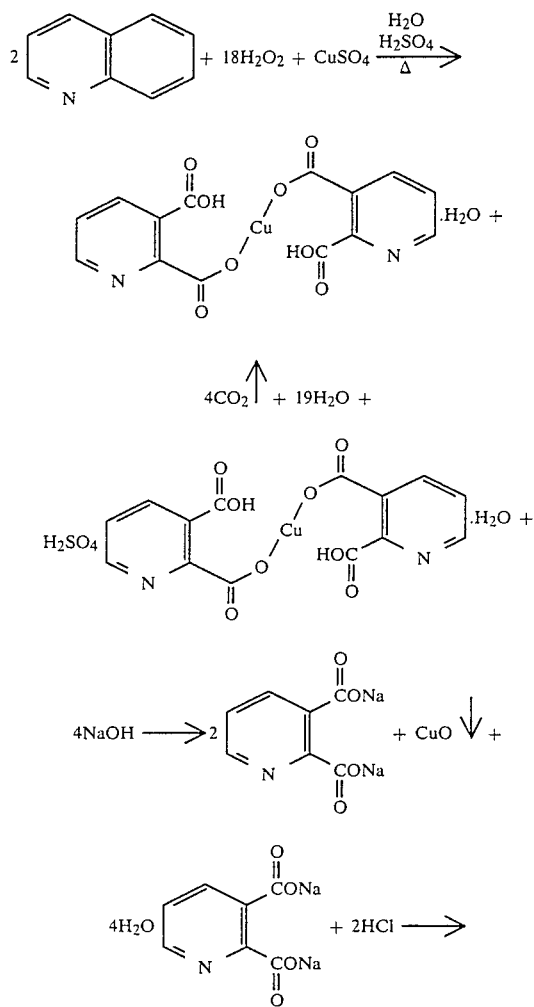

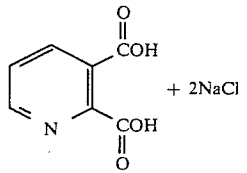

+ 2NaCl

Surprisingly, it has been found that by employing the improvements indicated above for the initial step, that is by adding separately in a portion-wise manner multiple (approximately 15 to approximately 25) approximately equal proportions of the reaction quantities of the sulfuric acid, the quinoline and the hydrogen peroxide sequentially in that order or simultaneously to an aqueous solution of the copper sulfate, at time intervals of sufficient length spaced between each group of portion-wise additions as to allow the hydrogen peroxide to react before the next addition to an unreacted hydrogen peroxide concentration in the reaction mixture of between approximately three percent and approximately fifteen percent, the quinoline is oxidized to obtain copper quinolinate in a very thermally controllable and safe manner and the formation of by-products is minimized. Alternatively, it has been found in the initial step that by continuously and simultaneously adding separately the reaction quantities of the sulfuric acid, the quinoline and the hydrogen peroxide to an aqueous solution of the copper sulfate at such a rate as to allow the hydrogen peroxide to react to maintain an unreacted hydrogen peroxide concentration in the reaction mixture of between approximately three and approximately fifteen percent, the quinoline is oxidized to obtain copper quinolinate in a very thermally controllable and safe manner and the formation of by-products in minimized. Further, it has been found that these improved processes can be used successfully on large commercial batch sizes as well as on small laboratory scale size reactions with the same excellent control of the exotherm and carbon dioxide evolution exhibited during the oxidation on either batch scale. By contrast, the synthetic processes taught in both the Stix et al. article and U.S. Pat. No. 2,371,691 are extremely difficult to control when scaled to batches larger than the laboratory size reactions described in the references let alone attempting to run them at a more concentrated water to quinoline ratio than those described in the references.

The two generally known prior art processes for the oxidation of quinoline and isolation of quinolinic acid were compared with applicants' instantly-claimed processes. Following the Stix et al. process, one molecular proportion of quinoline was mixed with a large volume of three percent aqueous hydrogen peroxide, which contained ten molecular proportions of hydrogen peroxide, and a volume of twenty-five percent sulfuric acid sufficient to contain 0.64 molecular proportion of sulfuric acid. The resulting solution was heated to 60° C., and an aqueous solution containing 1.4 molecular proportions of copper sulfate was added. The reaction mixture was heated slowly until carbon dioxide evolution began with a spontaneous rise in the reaction temperature. The reaction mixture was maintained at a temperature below 70° C. with great difficulty by means of an external cooling bath. After the vigorous exotherm had subsided, heat was applied to maintain 70° C. for eight hours, at which time an additional 0.175 molecular proportion of hydrogen peroxide was added and the stirring continued for three hours at a temperature of 65° to 70° C. After cooling to room temperature, the solid in the reaction mixture was separated by filtration and washed with water. The pH of the filtrate was adjusted to indicate a faint positive on Congo Red test paper using 50 percent sodium hydroxide and a second crop of solid was isolated by filtration. The two crops of solids were combined with water and 0.18 molecular proportion of sodium hydrosulfide and heated to approximately 90° C., cooled slightly, and filtered to remove the copper sulfide. The filtrate was evaporated to dryness to obtain 0.488 molecular proportion of solids, which after several recrystallizations from hot water failed to yield any quinolinic acid. The first step of this process has a water to quinoline ratio of ninety-two parts by weight of water to one part by weight of quinoline. This overall method is described in detail after the examples of the instantly-claimed invention.

Following the teaching of U.S. Pat. No. 2,371,691, one molecular proportion of quinoline was mixed with 1.4 molecular proportions of copper acetate and 3.2 molecular proportions of acetic acid in a large volume of water. After the resulting solution was heated to approximately 60° C., a volume of 35.0 percent aqueous hydrogen peroxide containing twelve molecular proportions of hydrogen peroxide was added at such a rate as to prevent the temperature from exceeding 70° C. whilst using external cooling to permit maintaining the addition rate. After the addition was complete, the reaction mixture was stirred for approximately three hours at 55° to 60° C. by which time the carbon dioxide evolution ceased. The resulting slurry was cooled and the solid collected by filtration and washed with water to obtain a water-wet filter cake containing copper quinolinate. An aliquot of the wet filter cake was dried in order to determine the percent of solids present in the filter cake. An aliquot of the water-wet filter cake based on the determined percent of solids was heated in an aqueous solution of ammonium hydroxide and sodium hydroxide to convert the copper quinolinate to sodium quinolinate and precipitate the copper in its oxide form. After removing the copper oxide by filtration, the filtrate was rendered acidic and the separated quinolinic acid was collected by filtration, washed and dried. The water to quinoline ratio of the first step of this process is fifty parts by weight of water to one part by weight of quinoline. This overall method is described in detail after the examples of the instantly-claimed invention.

The best mode contemplated by the inventors for carrying out this invention is now described as to enable any person skilled in the art to which it pertains to make and use the same.

The first of the process improvement aspects of the initial step of this invention is carried out by dissolving 0.5 molecular proportion of copper sulfate in water and heating the resulting solution to a temperature in the range of 50° to 60° C. While maintaining a temperature of 55° to 60° C., each of the following was added separately in a portionwise manner in fifteen to twenty-five portions (preferably twenty portions) one molecular proportion of quinoline, 2.5 molecular proportions of sulfuric acid and 11.5 molecular proportions of hydrogen peroxide sequentially in that order. The hydrogen peroxide can be in the form of any commercial aqueous solution. Particularly preferred are 35 or 50 percent solutions. Each group of additions is made at approximately equal time intervals depending on the amount of unreacted hydrogen peroxide present in the reaction from the preceding addition. The unreacted peroxide content in the reaction can be determined by any of numerous analytical methods known in the art. One such method of analysis is an iodine-iodide titration wherein an excess of potassium iodide is reacted in an acidic solution with a weighed sample of the reaction solution containing hydrogen peroxide which reduces the iodide ion to generate elemental iodine. The iodine is then analyzed by titrating the solution with a standardized solution of sodium thiosulfate, and the amount of hydrogen peroxide present in the original sample in calculated. It is preferred to wait until the unreacted hydrogen peroxide concentration in the reaction mixture is less than fifteen percent and it is particularly preferred to wait until the concentration is below ten percent before making the next set of additions. By allowing the hydrogen peroxide to react to a level in the reaction mixture of between three and fifteen percent between each of the portion-wise additions, the reaction is thermally controllable and the formation of by-products is minimized. After all of the additions are made, the reaction mixture is maintained at a temperature in the range of 55° to 60° C. until the unreacted hydrogen peroxide level has remained approximately constant for at least one hour. The reaction mixture is cooled to a temperature in the range of 20° to 25° C. and the copper quinolinate collected by filtration and washed acid free to Congo Red test paper with cold water. The copper quinolinate thus obtained is converted to quinolinic acid. The copper quinolinate is dissolved and heated in the presence of sodium hydroxide to precipitate the copper oxide which is separated by filtration. The filtrate is made acid and the quinolinic acid which precipitates is collected by filtration, washed with water and dried. Subsequently, the filtrate from the quinolinic acid isolation is treated with sufficient solid copper sulfate pentahydrate causing all of the dissolved quinolinic acid present in the filtrate to precipitate as copper quinolinate. The second crop of copper quinolinate is collected by filtration and subsequently recycled into future conversions to quinolinic acid. The filtrate from the recovery of copper quinolinate is treated with additional copper sulfate pentahydrate to determine if all of the quinolinic acid has been recovered through precipitation as copper quinolinate.

In this first process improvement aspect of the initial step of the invention, the ratio of overall water content of the reaction to quinoline is preferred to be within the range between approximately four and approximately fifteen parts by weight of water to one part by weight of quinoline.

The second of the process improvement aspects of the initial step of this invention is carried out by dissolving 0.5 molecular proportion of copper sulfate in water and heating the resulting solution to a temperature in the range of 50° to 65° C., preferably 55° to 60° C. Continuously and simultaneously over a period of 4 to 10 hours, 2.5 molecular proportions of sulfuric acid, one molecular proportion of quinoline and 11.5 molecular proportions of hydrogen peroxide are added separately to the warmed copper sulfate solution, preferably at the rate of 0.46 molecular proportion of sulfuric acid, 0.167 molecular proportion of quinoline and 1.92 molecular proportions of hydrogen peroxide per hour. During the continuous and simultaneous additions, the temperature of the reaction mixture is maintained in the range of 50° to 70° C., preferably 55° to 60° C., by means of external cooling. The rate at which the sulfuric acid, quinoline and hydrogen peroxide are added to the reaction mixture is determined by sampling the reaction mixture, preferably every hour after the continuous and simultaneous addition has started, and analyzing the sample for the percent of unreacted hydrogen peroxide in the manner described hereinabove. The percent of unreacted hydrogen peroxide should be maintained between three and fifteen percent and preferably between five and ten percent. By maintaining an unreacted hydrogen peroxide concentration of between three and fifteen percent in the reaction mixture, the reaction is thermally controllable and the formation of by-products is minimized. After all of the sulfuric acid, quinoline and hydrogen peroxide has been added to the reaction the temperature is maintained in the range of 50° to 65° C., preferably 55° to 60° C., until the unreacted hydrogen peroxide content in the reaction mixture does not change more than 0.4 to 0.5 percent in successive samplings from the reaction mixture. The reaction mixture is cooled to a temperature in the range of 20° to 25° C., maintained approximately one hour, and the copper quinolinate is collected by filtration and washed with water. The copper quinolinate thus obtained is converted to quinolinic acid in the manner described under the first improvement aspect detailed hereinabove.

In this second process improvement aspect of the initial step of the invention, the ratio of overall water content of the reaction to quinoline is preferred to be within the range between approximately four and approximately fifteen parts by weight of water to one part by weight of quinoline.

The hydrogen peroxide used in the first step of the process aspects of this invention can be of any commercial concentration but in view of the desirability for maintaining a low water to quinoline ratio, it is preferred to use a concentrated peroxide, for example, thirty-five or fifty percent active hydrogen peroxide.

The following examples will further illustrate the invention without the latter being limited thereby.

EXAMPLE 1

A. With stirring, 99.0 pounds (0.4 moles) of copper sulfate pentahydrate was added to 158.5 pounds of water and solution was effected by heating the mixture to a temperature in the range of 55° to 60° C. While maintaining the solution at a temperature in this range, the other reactants were introduced into the reaction in twenty equal portionwise additions spaced approximately one-half hour apart. Thus, each of the twenty additions consisted of 10.45 pounds (total 209.0 pounds; 1.98 moles) of 66° Be' sulfuric acid, 5.125 pounds (total 102.5 pounds; 0.79 moles) of quinoline and 31.0 pounds (total 620.0 pounds; 9.1 moles) of 50 percent aqueous hydrogen peroxide. These reactants were added separately and sequentially as listed. After all the additions were complete, the temperature of the reaction mixture was maintained in the range of 55° to 60° for approximately seven hours during the last hour of which the unreacted peroxide concentration in the reaction had remained essentially unchanged. The reaction mixture was cooled to approximately 20° C. and the solid which formed was collected by filtration and washed with three 25.0 gallon portions of water to obtain 282.0 pounds of water-wet copper quinolinate. A 100.0 g aliquot of the water-wet pulp was dried to obtain 35.75 g of copper quinolinate. Thus, the weight of the water-wet filter cake was projected to contain 100.8 pounds of copper quinolinate representing a 61.6 percent yield of copper quinolinate based on the quinoline charged.

B. A mixture of 579.6 ml of water and 36.1 g of sodium hydroxide pellets was heated to a temperature in the range of 90° to 95° C. with stirring and slowly, over approximately one-half hour, a 231.6 g portion of the water-wet copper quinolinate filter cake from part A above containing 82.8 g of copper quinolinate was added. The resulting slurry was maintained at a temperature in the range of 95° to 100° C. for approximately one hour, cooled to a temperature in the range of 20° to 25° C. and filtered and the filtrate set aside. The filter cake was washed with 124.2 ml of water and the water wash combined with the retained filtrate. The filter cake was dried to obtain 19.7 g of cupric oxide. The combined filtrate and wash was adjusted to a pH in the range of 1.4 to 1.6 by the gradual addition of 75.0 ml of concentrated hydrochloric acid whilst keeping the temperature below 25° C. by means of an external ice-water bath. The resulting slurry was stirred approximately one hour at a temperature in the range of 0° to 5° C. The separated solid was collected by filtration and the filtrate retained. The solid was dried in an air oven to obtain 52.3 g of product which assayed at 86.4 percent quinolinic acid by means of gas chromatographic analysis. Solid copper sulfate pentahydrate was added to the filtrate with stirring to precipitate the dissolved quinolinic acid. The copper sulfate pentahydrate was added until no additional solid separated from the solution. The separated solid was collected by filtration and dried to obtain as a second crop, 7.5 g of copper quinolinate which was retained for combination with subsequent batches of copper quinolinate. The overall assayed yield of quinolinic acid from quinoline taking into account the recovered copper quinolinate was 46.4 percent.

GAS CHROMATOGRAPHIC ANALYSIS OF QUINOLINIC ACID

The assayed percentages of quinolinic acid stated in Examples 1-3 contained herein is a determination of the purity of the product obtained in these examples by the method described hereinbelow.

A. Preparation of Sample

A 0.1 g sample of quinolinic acid is dissolved in 2.0 ml of pyridine and 2.0 ml of N,O-bis(trimethylsilyl)trifluoroacetamide. When the sample is completely dissolved 1.0 ml of a ten percent methyl-p-toluate solution in toluene is added to the sample solution.

B. Analysis

A 2.0 μl sample is injected into a Perkin-Elmer 900 gas chromatograph having a 6 ft. by ⅛ inch nickel tubing column packed with 10 percent OV101 on 80/100 mesh Gas-Chrom ®Q. The injection temperature is 300° C., column temperature is initially 100° C. programmed to increase at the rate of 10° C. per minute to a final temperature of 250° C., the detector temperature is 340° C. and the carrier gas is nitrogen.

EXAMPLE 2

A. A stirred solution of 103.2 pounds (0.42 mole) of copper sulfate pentahydrate in 660.0 pounds of water was heated to a temperature in the range of 55° to 60° C. Then, while maintaining the solution in this temperature range, the remaining reactants were added in a portionwise manner in twenty additions spaced approximately one-half hour apart. In each of the twenty additions, 11.08 pounds (total 221.6 pounds; 2.10 moles) of 66° Be' sulfuric acid, 5.36 pounds (total 107.2 pounds; 0.83 mole) of quinoline and 46.24 pounds (total 924.8 pounds; 9.5 moles) of 35 percent aqueous hydrogen peroxide were added separately and in the stated sequence. When the additions were complete, the reaction mixture was stirred for approximately eight and one-half hours at a temperature in the range of 55° to 60° C. during the last hour of which the unreacted peroxide concentration in the reaction remained approximately unchanged. The reaction mixture was cooled to approximately 20° C. and the solid which formed was collected by filtration and washed two times, each with 24.0 gallons of water to obtain 237.5 pounds of a waterwet filter cake containing copper quinolinate. A 100.0 g aliquot of the waterwet filter cake was dried at 60° C. to obtain 48.2 g of copper quinolinate. Thus, the weight of the water-wet filter cake was projected to contain 113.9 pounds of copper quinolinate which represented 66.3 percent yield based on the quinoline charged.

B. A mixture of 610.4 ml of water and 38.0 g of sodium hydroxide pellets was heated to a temperature in the range of 90° to 95° C. to effect solution and slowly, over approximately one-half hour, 180.9 g of water-wet copper quinolinate containing 87.2 g of copper quinolinate from part A above was added. The resultant slurry was maintained at a temperature in the range of 95° to 100° C. for approximately one hour and cooled to a temperature in the range of 20° to 25° C. by means of an ice-water bath. The solid was collected by filtration, washed with 130.8 ml of water and dried to obtain 20.4 g of cupric oxide. The combined filtrate and water wash was adjusted slowly to a pH in the range of 1.4 to 1.6 with the addition of 74.0 ml of concentrated hydrochloric acid while maintaining the temperature below 25° C. The resulting slurry was then chilled for approximately one hour at a temperature in the range of 0° to 5° C. The separated solid was collected by filtration and dried to obtain 52.5 g of product which assayed at 88.0 percent quinolinic acid by gas chromatography. Solid copper sulfate pentahydrate was added gradually to the filtrate from the quinolinic acid filtration until no additional solid formed. The resulting slurry was stirred approximately one hour at ambient temperature. The separated solid was collected by filtration and dried to obtain a second crop of 14.0 g of recovered copper quinolinate to be used in subsequent conversions to quinolinic acid. The overall yield from quinoline to quinolinic acid taking into account the recovered copper quinolinate was 51.8 percent.

EXAMPLE 3

A. In a 500.0 gallon reactor a solution of 300.0 pounds (1.2 moles) of copper sulfate pentahydrate dissolved in 1293.0 pounds of water was heated to a temperature in the range of 55° to 60° C. with stirring. Separately and simultaneously, 633.0 pounds (6.0 moles) of 93 percent sulfuric acid, 310.0 pounds (2.4 moles) of quinoline and 1879.0 pounds (27.6 moles) of 50 percent hydrogen peroxide were added continuously to the solution at the following rates: 79.1 pounds of 93 percent sulfuric acid per hour; 38.6 pounds of quinoline per hour; and 234.9 pounds of 50 percent hydrogen peroxide per hour. The additions required approximately eight hours during which the reaction temperature was held in the range of 56° to 62° C. by means of circulating the reaction mixture through an external heat exchanger. Every hour during the simultaneous and continuous additions, a small sample of the reaction mixture was removed and titrated for the concentration of unreacted hydrogen peroxide present. If the unreacted peroxide level exceeded ten percent in the reaction mixture, the simultaneous additions were stopped momentarily until the level dropped below ten percent. After all of the sulfuric acid, quinoline and hydrogen peroxide were added, the reaction mixture was stirred at a temperature in the range of 55° to 60° C. until the unreacted hydrogen peroxide level did not change more than 0.4 to 0.5 percent over a period of one hour. This required stirring approximately an additional seven hours at a temperature of 55° to 60° C. The reaction mixture was then cooled to a temperature in the range of 20° to 25° C. and maintained in that for approximately one hour. The separated solid was collected by filtration and washed with water to obtain 622.0 pounds of water-wet filter cake. A 200.0 g aliquot of the water-wet filter cake was dried to obtain 105.2 g of copper quinolinate. Thus, the weight of the water-wet filter cake was projected to contain 327.0 pounds of copper quinolinate which represented a 65.8 percent yield based on the quinoline charged.

B. In a 1000 gallon reactor a solution of 3435.0 pounds of water and 770.0 pounds of flake sodium hydroxide was heated to a temperature in the range of 80° to 90° C. Slowly, over approximately one hour, the 622.0 pounds of water-wet copper quinolinate from part A above and an additional 2387.0 pounds of water-wet copper quinolinate made in manner similar to that described in part A above totaling 1494.0 pounds of dry copper quinolinate prepared from 1638.0 pounds of quinoline was added to the hot sodium hydroxide solution. The resulting slurry was maintained at a temperature in the range of 95° to 100° C. for approximately one hour. The slurry was cooled to approximately 75° C. and the separated solid was collected by filtration and washed with a solution of 5.0 pounds of flake sodium hydroxide dissolved in 500.0 pounds of water to obtain 587.0 pounds of wet cupric oxide which was 52.2 percent solids. The combined filtrate and alkaline wash was added slowly to 1450.0 pounds of 20° Be' hydrochloric acid. The pH of the resulting slurry was adjusted to 1.4 by adding an additional 584.0 pounds of 20° Be' hydrochloric acid. The slurry was cooled to approximately 25° C., the solid collected by filtration and dried to obtain 1101.0 pounds of product which assayed at 96.0 percent quinolinic acid by gas chromatography. This represents 1056.9 pounds of 100 percent quinolinic acid. To the acidic filtrate from the quinolinic acid isolation, solid copper sulfate pentahydrate was added slowly precipitating the dissolved quinolinic acid as copper quinolinate. The slow addition of copper sulfate continued until no further precipitation occurred. An aliquot of the resulting slurry was tested by removing the solid by filtration and adding copper sulfate to the filtrate. When no additional precipitate formed, sufficient copper sulfate had been added. After stirring the slurry for approximately one hour, the solid was collected by filtration and washed with water to obtain 198.0 pounds of water-wet filter cake, which contained after drying a second crop of 118.8 pounds of recovered copper quinolinate. The overall yield of quinolinic acid from quinoline taking into account the recovered copper quinolinate was 49.8 percent.

COMPARATIVE EXAMPLE I

Following the procedure described in Chemische Berichte 65, 11 (1932), a mixture of 1890.0 ml of water, 210.0 ml of 30 percent hydrogen peroxide, 7.0 ml of 100 percent sulfuric acid and 24.0 g of quinoline was heated to 60° C. with stirring. A solution of 64.0 g of copper sulfate pentahydrate dissolved in 160.0 ml of water was added rapidly to the mixture causing the temperature to rise to 62° C. The resultant mixture was heated to 65° C. at which temperature there was a vigorous evolution of gas and the temperature was maintained between 65° and 70° C. with great difficulty by the use of external cooling. After approximately one hour, a green solid started forming in the reaction mixture. After an additional one-half hour, the evolution of gas ceased and external heat was required to maintain a temperature in the range of 65° to 70° C. for an additional one and one-half hours. Twenty milliliters of 30 percent hydrogen peroxide was added and an exotherm and gas evolution resulted. The temperature was maintained in the range of 65° to 70° C. for an additional three hours. Sodium bicarbonate was added slowly to the reaction mixture until the mixture gave a faint test for acidity on Congo Red test paper. During the bicarbonate addition the temperature rose to 90° C. The resulting mixture was allowed to cool to ambient temperature overnight with stirring. The solid was collected by filtration, washed with 50.0 ml of water and dried to obtain 18.4 g of a solid. The filtrate was adjusted with sodium bicarbonate until it tested neutral to both Brilliant Yellow test paper and Congo Red test paper, heated to approximately 90° C., and subsequently cooled to ambient temperature. The solid which formed was collected by filtration and dried to obtain 7.6 g of a solid. The combined, dry solids were suspended in 200.0 ml of water and 10.0 g of sodium sulfide was added. The resulting mixture was heated to approximately 90° C. with stirring and filtered. The filtrate was evaporated to dryness to obtain 15.2 g of a brown solid. The brown solid was recrystallized twice from hot water yielding a tan-colored solid. Examination of the product by thin layer chromatography determined the product to be predominantly salts with a small amount of organic matter including traces of quinolinic acid.

COMPARATIVE EXAMPLE II

A. In a 50 gallon glass-lined reactor a mixture of 51.1 pounds of water, 23.4 pounds (0.39 mole) of glacial acetic acid and 7.2 pounds (0.09 mole) of cupric oxide was maintained at a temperature in the range of 98° to 100° C. for approximately thirteen hours to prepare a slurry of copper acetate. The slurry was cooled to ambient temperature and with stirring and 108.6 pounds of water and 8.3 pounds (0.064 mole) of quinoline were added to the resulting slurry. The mixture was heated to a temperature in the range of 60° to 65° C. and 1.0 pound of 35 percent hydrogen peroxide was added resulting in the evolution of carbon dioxide. Slowly, over approximately one hour and forty-five minutes, 85.0 pounds (0.875 mole) of 35 percent hydrogen peroxide was added. Initially the reaction mixture exhibited an exotherm to 68° C. in spite of external cooling, the reaction mixture was maintained at a temperature in the range of 60° to 65° C. by controlling the rate of addition and the external cooling. After approximately 60.0 pounds of the 35 percent hydrogen peroxide was added to the reaction mixture the temperature had dropped to 57° C. The rate of the peroxide addition was increased slightly and the reaction mixture exothermed to 76° C. To bring the reaction under control, approximately 25.0 pounds of cold water was added directly into the reaction mixture. The peroxide addition was continued, and when completed, the temperature was maintained at 60° to 65° C. for approximately two hours. After cooling the reaction mixture to ambient temperature, the solid was collected by filtration and washed with cold water to obtain 20.0 pounds of water-wet copper quinolinate. A 100.0 g sample of the water-wet copper quinolinate yielded 65.52 g of solids when dried. This projects to a copper quinolinate weight of 13.1 pounds which is 77.06 percent yield based on the quinoline.

B. With stirring a mixture of 769.0 g of water-wet copper quinolinate from part A above (500.0 g of dry), 731.0 g of water, 556.0 ml of commercial ammonium hydroxide and 253.0 ml of 50 percent aqueous sodium hydroxide was maintained at a temperature in the range of 65° to 70° C. for approximately one hour. The solid cupric oxide that formed was collected by filtration and washed with 200.0 ml of hot water. The combined filtrate and water wash was maintained at a temperature in the range of 90° to 95° C. for sufficient time to boil the ammonia from the solution. The pH of the solution was adjusted to 1.4 to 1.6 by the addition of 20° Be' hydrochloric acid. The resulting mixture was placed in a freezer at approximately −2° C. for approximately 18 hours. The solid which formed was collected by filtration and dried to obtain 86.5 g of quinolinic acid. The filtrate was concentrated from 2500.0 ml to 1500.0 ml but no additional product was obtained.

The overall yield of quinolinic acid from quinoline was 21.2 percent.

COMPARATIVE EXAMPLE III

A. In a 200 gallon glass-lined reactor a mixture of 885.1 pounds of water, 74.0 pounds (1.23 moles) of glacial acetic acid, 106.0 pounds (0.53 mole) of cupric acetate and 49.0 pounds (0.38 mole) of quinoline was heated with stirring to a temperature in the range of 55° to 60° C. Slowly over approximately six hours, 500.0 pounds (5.15 moles) of 35 percent hydrogen peroxide was added to the mixture while maintaining a temperature in the range of 55° to 60° C. by means of external cooling and the rate of the peroxide addition. The reaction mixture was stirred ninety minutes at a temperature in the range of 55° to 60° C. After an additional eight hours of stirring the temperature in the reaction mixture was 45° C. The slurry was cooled to approximately 20° C. and the solid was collected by filtration and washed with water to obtain 163 pounds of water-wet copper quinolinate. A 100.0 g sample of the water-wet filter cake was dried to obtain 45.7 g of solids. This projects to 74.5 pounds of dry copper quinolinate which is a 74.0 percent yield based on the quinoline.

B. In a 200.0 gallon stainless steel reactor a mixture of 146.9 pounds of water, 191.0 pounds of commercial ammonium hydroxide and 426.0 pounds of water-wet copper quinolinate containing 191.0 pounds of dry copper quinolinate including the copper quinolinate from part A above, and the remainder made in a manner similar to part A above was stirred until a complete solution was obtained. Slowly, 162.0 pounds of 50 percent aqueous sodium hydroxide was added to the solution. The resulting solution was heated to and maintained at a temperature in the range of 65° to 70° C. for approximately six hours. The solid, which precipitated, was collected by filtration, washed with a small amount of hot water, and dried to obtain 79.0 pounds of cupric oxide. The filtrate and wash were combined and maintained at a temperature in the range of 80° to 90° C. until all of the ammonia had been removed from the solution, approximately eight hours. The solution was cooled to a temperature in the range of 20° to 30° C. and 51.0 pounds of 20° Be' hydrochloric acid was added adjusting the pH to 7.0. The mixture was chilled to 0° to 5° C. and an additional 96.0 pounds of hydrochloric acid was added lowering the pH to 1.4. After stirring overnight at ambient temperature the solid was collected by filtration and dried to obtain 15.0 pounds of quinolinic acid. To the filtrate an additional 28.0 pounds of 20° Be' hydrochloric acid was added lowering the pH to 0.8. Approximately 6.0 pounds of sodium acetate was added to the solution adjusting the pH to approximately 1.5. The resulting suspension was cooled to −5° C., and stirred approximately one hour. The solid was collected by filtration and dried to obtain an additional 58.0 pounds of quinolinic acid. This represented a 60.6 percent yield based on the copper quinolinate charged. The overall yield of quinolinic acid was 38.4 percent based on a total of 147.0 pounds of quinoline charged.

We claim:

1. In a process wherein quinoline is oxidized in an initial step with hydrogen peroxide in an aqueous medium in the presence of sulfuric acid and copper sulfate to produce copper quinolinate and in subsequent steps, the copper quinolinate is treated with alkali to convert said copper quinolinate to its soluble alkali salt form which is removed from the insoluble cupric oxide and thereafter said soluble alkali salt form is treated with acid to produce quinolinic acid, the improvement whereby the reaction of the initial step is carried out in a thermally controllable and safe manner and the formation of by-products is minimized which comprises adding separately in said initial step in a portion-wise manner approximately fifteen to approximately twenty-five approximately equal portions of the reaction quantities of the sulfuric acid, the quinoline and the hydrogen peroxide either sequentially in that order or simultaneously at time intervals of sufficient length spaced between each group of portion-wise additions as to allow the hydrogen peroxide to react before the next addition to an unreacted hydrogen peroxide concentration in the reaction mixture of between approximately three and approximately fifteen percent.

2. In a process according to claim 1 wherein the improvement further comprises utilizing in the initial step a ratio of from approximately four parts to approximately fifteen parts by weight of water for each part by weight of quinoline in the aqueous medium of the reaction.

3. In a process wherein quinoline is oxidized in an initial step with hydrogen peroxide in an aqueous medium in the presence of sulfuric acid and copper sulfate to produce copper quinolinate and in subsequent steps, the copper quinolinate is treated with alkali to convert said copper quinolinate to its soluble alkali salt form which is removed from the insoluble cupric oxide and thereafter said soluble alkali salt form is treated with acid to produce quinolinic acid, the improvement whereby the reaction of the initial step is carried out in a thermally controllable and safe manner and the formation of by-products is minimized which comprises continuously and simultaneously adding separately in the initial step the reaction quantities of the sulfuric acid, the quinoline and the hydrogen peroxide to an aqueous solution of the copper sulfate at such a rate as to allow the hydrogen peroxide to react to maintain an unreacted hydrogen peroxide concentration in the reaction of between approximately three and approximately fifteen percent.

4. In a process according to claim 3 wherein the improvement further comprises utilizing in the initial step a ratio of from approximately four parts to approximately fifteen parts by weight of water for each part by weight of quinoline in the aqueous medium of the reaction.

5. In a process wherein quinoline is oxidized with hydrogen peroxide in an aqueous medium in the presence of sulfuric acid and copper sulfate to produce copper quinolinate, the improvement whereby the reaction is carried out in a thermally controllable and safe manner and the formation of by-products is minimized which comprises adding separately in a portion-wise manner approximately fifteen to approximately twenty-five approximately equal portions of the reaction quantities of the sulfuric acid, the quinoline and the hydrogen peroxide either sequentially in that order or simultaneously, at time intervals of sufficient length spaced between each group of portion-wise additions as to allow the hydrogen peroxide to react before the next addition to an unreacted hydrogen peroxide concentration in the reaction mixture of between approximately three and approximately fifteen percent.

6. In the process according to claim 5 wherein the improvement further comprises utilizing a ratio of from approximately four parts to approximately fifteen parts by weight of water for each part by weight of quinoline in the reaction.

7. In the process wherein quinoline is oxidized with hydrogen peroxide in an aqueous medium in the presence of sulfuric acid and copper sulfate to produce copper quinolinate, the improvement whereby the reaction is carried out in a thermally controllable and safe manner and the formation of by-products is minimized which comprises continuously and simultaneously adding separately the reaction quantities of the sulfuric acid, the quinoline and the hydrogen peroxide to an aqueous solution of the copper sulfate at such a rate as to allow the hydrogen peroxide to react to maintain an unreacted hydrogen peroxide concentration in the reaction of between approximately three and approximately fifteen percent.

8. In the process according to claim 7 wherein the improvement further comprises utilizing a ratio of from approximately four parts to approximately fifteen parts by weight of water for each part by weight of quinoline in the aqueous medium of the reaction.

* * * * *